(12) United States Patent
Michelsen et al.

(10) Patent No.: US 6,355,792 B1
(45) Date of Patent: Mar. 12, 2002

(54) METHOD FOR ISOLATING AND PURIFYING NUCLEIC ACIDS

(75) Inventors: Uwe Michelsen, Weinheim; Karl Holschuh, Seeheim-Jugenheim; Robertus Hendriks, Heidelberg, all of (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/601,397

(22) PCT Filed: Jan. 22, 1999

(86) PCT No.: PCT/EP99/00413

§ 371 Date: Aug. 2, 2000

§ 102(e) Date: Aug. 2, 2000

(87) PCT Pub. No.: WO99/40098

PCT Pub. Date: Aug. 12, 1999

(30) Foreign Application Priority Data

Feb. 4, 1998 (DE) .......................... 198 04 243

(51) Int. Cl.[7] ..................... C07H 21/00; C07H 21/02; C07H 21/04
(52) U.S. Cl. .................... 536/25.4; 536/25.41
(58) Field of Search .............. 536/25.4, 25.41

(56) References Cited

U.S. PATENT DOCUMENTS 5,693,785 A * 12/1997 Woodard et al. ........... 536/25.4
5,973,138 A * 10/1999 Collis ..................... 536/25.41

FOREIGN PATENT DOCUMENTS

| DE | 43 21 904 | 1/1995 |
| EP | 0 818 461 | 1/1998 |
| EP | 0818461 A2 * | 1/1998 |
| EP | 0 897 978 | 2/1999 |
| WO | 96 41811 | 12/1996 |

OTHER PUBLICATIONS

Sambrook et al. 1989. Molecular Cloning, a Laboratory Manual, Second Edition. Cold Spring Harbor Laboratory Press. pp. B.20–B.28.*

* cited by examiner

*Primary Examiner*—Remy Yucel
*Assistant Examiner*—Konstantina Katcheves
(74) *Attorney, Agent, or Firm*—Millen, White, Zelano & Branigan, P.C.

(57) ABSTRACT

The invention provides a method for isolating and purifying nucleic acids from liquid samples. The method comprises using a solid carrier which is essentially made of oxide inorganic materials containing hydroxyl groups (e.g., silica gel or hydroxylapatite). The nucleic acids are bound to the carrier material in the acidic pH range while they are eluted in the alkaline pH range.

11 Claims, 1 Drawing Sheet

METHOD FOR ISOLATING AND PURIFYING NUCLEIC ACIDS

The invention relates to a process for the isolation and purification of nucleic acids from liquids with the aid of a solid carrier material.

An extensive prior art exists which describes the isolation of nucleic acids from body fluids. Older methods comprise several working steps: enrichment of the nucleic acid-containing cells or compartments, lysis thereof, separation of the protein and membrane fractions, precipitation of the purified nucleic acids for the removal of contaminating chemicals. More recent methods use solid-phase extractions, the nucleic acid-containing compartments being lysed under specific reaction conditions and DNA and RNA or their subpopulations being bound to the solid phase. Specific reaction conditions are high molar concentrations of specific chaotropic substances or of water-soluble organic solvents. High molecular weight, genomic DNA of eukaryotic cells can likewise be captured and purified by simple lysis of the cells by means of detergence and physical interaction of the long DNA threads with microparticles or large-pore filters. It is also known that purified nucleic acids bind to chromatographic material such as hydroxyapatite in aqueous medium and can be removed using relatively high molar phosphate buffer.

U.S. Pat. No. 5,234,809 discloses a process for the isolation of nucleic acids, the binding to a solid phase taking place in the presence of high concentrations of chaotropic substances such as guanidinium salts, sodium iodide, sodium thiocyanate or urea. The bound nucleic acids are washed with a wash buffer comprising a chaotropic substance. For the removal of the highly concentrated salts, washing is then carried out with an alcohol- and/or acetone-containing wash solution. After careful removal of the organic solvents, the nucleic acids are eluted with water or with buffer of low ionic strength. Similar processes are disclosed in EP 0 572 907.

According to WO 96/18731, the binding to the solid phase should take place under neutral buffer conditions in the presence of detergents. However, the process has the disadvantage that only long-chain DNA molecules such as genomic DNA of eukaryotic cells can be bound to the solid phase. Short DNA molecules and RNA molecules cannot be directly isolated under the buffer conditions described.

The described methods for the isolation and purification of nucleic acids have a number of disadvantages. Chaotropic substances in high concentrations, organic solvents and detergents have an inhibitory effect on subsequent molecular-biological reactions for whose purpose the nucleic acids are isolated. Intensive washing steps or drying steps are necessary in order to remove these inhibitors quantitatively. The described chemicals and washing steps are also a hindrance to automation plans with the aim of rapidly and reproducibly isolating gene material from a high number of samples.

WO 97/34909 discloses a process for the isolation of nucleic acids in which the nucleic acids from the sample are bound to an organic crosslinked polymer which has basic groups. For this binding step, additions of detergents, chaotropic substances or organic solvents are not necessary. However, binding takes place slowly and requires incubation times of one hour or more.

It is thus the object to make available a process for the isolation and purification of nucleic acids which can be carried out without interfering addition of the substances mentioned (e.g. chaotropic substances), and which requires a short incubation time. The isolated or purified nucleic acids (DNA and RNA) should be able to be employed for molecular-biological reactions immediately after elution from the solid phase.

It has been found that, when using inorganic oxide materials containing hydroxyl groups, binding of nucleic acids to these carrier materials is possible even without addition of chaotropic substances if the pH is lowered to 1 to 6 by the binding buffer. This binding takes place rapidly, i.e. within less than 15 minutes. After an optional washing step, the nucleic acid can be dissolved by means of an elution buffer having a pH of between 7.5 and 11 and is ready for further molecular-biological reactions.

The invention relates to a process for the isolation and purification of nucleic acids from liquid samples, characterized by the following process steps:

a) provision of a liquid sample which contains nucleic acids;

b) provision of a carrier material consisting of an inorganic oxide material containing hydroxyl groups;

c) dilution of the sample from step a) with a binding buffer;

d) treatment of the sample from step c) acidified by means of a binding buffer with the carrier material from step b), the nucleic acids being bound;

e) separation of the sample and of the binding buffer after binding of the nucleic acids;

f) elution of the nucleic acids bound in step d) by means of an alkaline solution.

In preferred embodiments, a washing step e1) is inserted after step e), the pH of the wash buffer used here being $\leq 6.5$. In further preferred embodiments, the pH of the binding buffer is between 3 and 6 and of the elution buffer from 7.5 to 9. Preferred carrier materials are silica gel and hydroxyapatite.

The invention further relates to reagent combinations for the process according to the invention for the isolation and purification of nucleic acids from liquid samples. In preferred embodiments, these reagent combinations contain all constituents necessary for carrying out the process: carrier material, binding buffer, one or more wash buffers and elution buffers. However, it is also possible to supply individual components of these separately, or to leave the obtainment of these components to the user, such that reagent combinations, for example, without the wash buffer are also a subject of the invention. Thus a reagent combination according to the invention can also comprise two or three constituents selected from carrier material, binding buffer, wash buffer and elution buffer, in particular comprise, for example, carrier material and binding buffer. Reagent combinations for the process according to the invention can further additionally contain auxiliaries such as centrifuge tubes or metering aids.

In FIG. 1, the binding kinetics for the process according to the invention (curves (A) and (B)) are compared with a process corresponding to the prior art according to WO 97/34909 (curves (C) and (D)). For the measured results shown in curves (B) and (D), bovine serum albumin was added to the sample in order to simulate the use of the processes for protein-containing samples. Further experimental details are found in the description for Comparative Example A.

As carrier materials, suitable inorganic oxide materials containing hydroxyl groups are known from the prior art, for example from U.S. Pat. No. 5,234,809; these include, in particular, crystalline or amorphous modifications of $SiO_2$ and silicates, i.e., for example, silica gel, kieselguhr, silicate glasses or zeolites, furthermore also hydroxyapatites. Preferred carrier materials are crystalline or amorphous modifications of $SiO_2$ and silicates.

The carrier materials can be present in the form of beads, particles, sheets, gels, filters, membranes, fibres, in capillaries, strips, tubes, microtitre plates etc. Appropriate magnetic particles can also be used. The carrier materials can also be applied, for example, as a coating to vessels. An equilibration buffer used for the carrier material is preferably one of the binding buffers mentioned below.

The binding of the nucleic acids from the sample is carried out by means of simple lowering of the pH to below pH 6. For this, a binding buffer is used which can maintain a pH range from 1 to 6, preferably from 3 to 5. As is known, the purine bases of the nucleic acids have improved stability in the preferred pH range. Suitable buffers are, for example, formate, acetate, citrate buffers or other buffer systems which have adequate buffer capacity in the pH range mentioned.

The buffer concentration should be in the range from 10 to 200 mM, depending on the buffer capacity of the sample liquid to be investigated. Preferably, a binding buffer of concentration of 50 mM is used which has a pH of about 4.5, e.g. a buffer consisting of acetic acid which has been adjusted to a pH of between 4 and 5 using sodium hydroxide solution, potassium hydroxide solution or using tris base. Nuclease inhibitors can be added to the binding buffer; suitable nuclease inhibitors are known to the person skilled in the art.

A binding buffer according to the present invention contains neither phosphate ions nor other ions in high concentrations (>200 mM), nor ionic detergents or chaotropic substances.

The nucleic acid-containing samples are aqueous liquids, such as buffer solutions and homogenates, or complex biological fluids, such as blood, serum, plasma, urine etc. or tissue and cell lysates.

The carrier material with the nucleic acids bound thereto can be washed with the described binding buffer or with other phosphate-free buffers, where the pH of this buffer should be between 4 and 7, preferably between 4.5 and 6.5. The buffer concentration can be lower than the binding buffer; it should be in the range from 5 to 50 mM, preferably approximately 8 to 15 mM. If appropriate, one of the wash buffers can contain additives, for example chelating agents such as EDTA, chaotropic substances and/or non-ionic detergents. The wash buffers disclosed according to the invention do not elute the bound nucleic acids even if these have been adsorbed on the carrier material with addition of chaotropic substances. In a wash buffer according to the present invention, additions of organic solvents and/or chaotropic substances are not necessary in order to avoid the premature elution of nucleic acids. However, additions of the mentioned auxiliaries are necessary in the process according to U.S. Pat. No. 5,234,809 in order to avoid the premature elution of nucleic acids. In connection with the present invention, additions of this type can be used in order to purify the isolated nucleic acid preparations, for example in order to wash out adsorbed proteins from the support. Additives suitable for purposes of this type and their concentrations are familiar to the person skilled in the art.

Surprisingly, it has been found that the nucleic acid purified in this way can be dissolved from the solid phase by a simple increase in the pH to above 7.5. The elution buffer used for this should maintain a pH range from 7.5 to 9, preferably 8 to 8.5. Suitable buffers are, for example, tris HCl buffer, tricine, bicine and other buffers which buffer in this pH range, preferably tris/HCl. The buffer concentration should be 5 to 10 mM, preferably approximately 8 to 10 mM. If appropriate, the elution buffer can contain chelating agents such as EDTA and/or other inhibitors of nucleases. The eluted nucleic acid is employable directly, without further purification steps, for molecular-biological applications, such as, for example, for amplification reactions.

The process for the isolation and purification of nucleic acids is carried out according to the present invention in such a way that, for example, a serum comprising the nucleic acids is mixed with the binding buffer and added to a microcentrifuge tube which already contains the equilibrated solid phase. After an incubation time, it is centrifuged and the supernatant is discarded. Resuspension is carried out using a wash buffer, the mixture is centrifuged again and the supernatant is discarded again. A number of washing steps, if appropriate with wash buffers of different composition, can also be carried out successively. Accordingly, a reagent combination according to the invention can also contain a number of wash buffers. Finally, the elution buffer is added, the suspension is centrifuged and the nucleic acid-containing supernatant is transferred to a new empty tube. This solution can then be employed directly for further analytical methods (PCR, NASBA). When using, for example, appropriate magnetic beads, the centrifugation can be replaced by the application of a magnetic field.

Even without further details, it is assumed from this that a person skilled in the art can utilize the above description to the widest extent. The preferred embodiments and examples are therefore only to be interpreted as descriptive, but in no way as in any manner limiting disclosure.

The complete disclosure of all applications, patents and publications mentioned above and below, and of the corresponding application DE 198 04 243.4, filed on Apr. 2, 1998, are inserted into this application by means of reference.

EXAMPLE 1

Materials

| Microcentrifuge tubes | |
|---|---|
| Binding buffer (BB): | 50 mM acetic acid/KOH, pH 4.5 |
| Wash buffer (WB): | 10 mM tris HCl, pH 6.5 |
| Elution buffer (EB): | 10 mM tris HCl, 1 mM EDTA, pH 9.0 |
| DNA or RNA: | 1 ng - 1 µg |
| Particles: | 0.5 g in 1 ml of 10 mM tris HCl, pH 6.5 |

Process steps 1. 80 µl of BB, 1 ng–1 µg of DNA/RNA, 1 µl of particles (500 mg/ml) are made up to 100 µl with water, 2. the mixture is incubated at room temperature for 5 minutes, 3. it is centrifuged at 5000 rpm for 10 seconds, the supernatant is discarded, 4. the particles are resuspended with 200–500 µl of WB, 5. steps 3 and 4 are repeated, 6. step 3 is repeated, 7. 30 µl of EB are added, 8. it is centrifuged at 5000 rpm for 10 seconds, the supernatant is transferred to a new tube.

Various particles are employed: hydroxyapatite (Merck item #1.05119) and silica particles (Merck item 1.01193). These are tested with and without addition of serum to the binding buffer. The concentration of radio-labelled lambda DNA per test corresponds to approximately 1 ng. The radioactivity is indicated in cpm·1000.

| Sample No. | Pipetting scheme [μl] | | | | | |
|---|---|---|---|---|---|---|
| | 1 | 2 | 3 | 4 | K1 | K2 |
| Particles: H: Hydroxyapatite S: Silica gel | H | S | H | S | | |
| Binding buffer (μl) | 80 | 80 | 80 | 80 | 80 | 80 |
| Serum (μl) | | | 10 | 10 | | |
| Water (μl) | 10 | 10 | | | 11 | 11 |
| P-32 λ-DNA (μl) | 9 | 9 | 9 | 9 | 9 | 9 |
| Particles (μl) | 1 | 1 | 1 | 1 | | |

| Sample No. | Results | | | | | |
|---|---|---|---|---|---|---|
| | 1 | 2 | 3 | 4 | K1 | K2 |
| Supernatant [cpm] | 22 | 14 | 7 | 17 | 179 | 173 |
| Bound [cpm] | 154 | 162 | 169 | 159 | | |
| 1st elution [cpm] 5 min., tris buffer pH 9 | 114 | 132 | 94 | 139 | | |
| 2nd elution [cpm] Phosphate buffer pH 7 | 36 | 4 | 56 | 1 | | |
| Remainder on particles [cpm] | 5 | 16 | 7 | 4 | | |
| Binding capacity [%] | 88 | 92 | 96 | 90 | | |
| Elution efficiency [%] | | | | | | |
| 1st elution | 74 | 81 | 55 | 87 | | |
| 2nd elution | 97 | 83 | 88 | 88 | | |

The particles utilized here having very different chemical groups on the surface bind 80 to 96% of the labelled DNA under the chosen conditions. As a rule, over 80% of the bound DNA is eluted again by simple pH change (e.g. tris buffer). A high molar phosphate buffer (0.5 M) improves the elution efficiency in the case of the hydroxyapatite particles.

When using appropriate magnetic particles, the centrifugation is replaced by the application of a magnetic field.

EXAMPLE 2

According to Example 1, a nucleic acid-containing sample (1 μg) is mixed with increasing amounts of serum. To increase the buffer capacity, the binding buffer is employed in 4 times concentrated form (=200 mM) at high serum concentrations. The yield is determined in agarose gels by means of ethidium bromide-stained nucleic acid bands. Silica particles are used as a carrier material.

| Serum [μl] | 0 | 10 | 20 | 30 | 50 |
|---|---|---|---|---|---|
| 1 × BB [μl] | 80 | 80 | 70 | — | — |
| 4 × BB [μl] | — | — | — | 50 | 40 |
| Yield of DNA or RNA | +++ | ++++ | ++++ | ++++ | +++ |

The results show that the binding of the nucleic acids to silica particles is independent of the serum concentration.

The above experiment is repeated using hydroxyapatite particles instead of the silica particles; even when using hydroxyapatite, similar results are obtained.

EXAMPLE 3

According to Example 1, various buffers having various pHs are employed and their suitability as binding buffers is tested. Silica particles are used as a carrier material. DNA and RNA (ribosomal yeast RNA) is employed in a final concentration of 0.5 μg. The yield of the eluate is determined in agarose gels by means of ethidium bromide-stained nucleic acid bands.

| Sample No. Binding buffer | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Pipetting scheme [μl] | | | | | | | | | | | | | | |
| Acetate/KOH pH 4.5 | 80 | 80 | | | | | | | | | | | | |
| Acetate/KOH pH 5.0 | | | 80 | 80 | | | | | | | | | | |
| Acetate/NaOH pH 4.5 | | | | | 80 | 80 | | | | | | | | |
| MES pH 5.5 | | | | | | | 80 | 80 | | | | | | |
| MES pH 6.0 | | | | | | | | | 80 | 80 | | | | |
| MES pH 6.5 | | | | | | | | | | | 80 | 80 | | |
| Tris HCl pH 7.0 | | | | | | | | | | | | | 80 | 80 |
| Water | 15 | 15 | 15 | 15 | 15 | 15 | 15 | 15 | 15 | 15 | 15 | 15 | 15 | 15 |
| DNA/RNA | 4 | 4 | 4 | 4 | 4 | 4 | 4 | 4 | 4 | 4 | 4 | 4 | 4 | 4 |
| Particles (500 mg/ml) | 1 | 1 | 1 | 1 | 1 | 1 | 1 | 1 | 1 | 1 | 1 | 1 | 1 | 1 |
| Results | | | | | | | | | | | | | | |
| Yield in % | 90 | 90 | 80 | 80 | 90 | 90 | 70 | 70 | 50 | 50 | 20 | 20 | 2 | 2 |

The yields obtained were achieved independently of the carrier material. The highest yields were obtained at pH 4.5.

The experiment is repeated using. hydroxyapatite particles instead of the silica particles; similar results to those compiled above are obtained.

Comparative Example A

In a comparative experiment, the binding kinetics of the process according to the invention were compared with the process using a basic organic polymer. For this, 1 μg of λ Hind III DNA ($^{32}$P-labelled; about 100,000 cpm) in 50 mM potassium acetate, pH 4.5, with and without addition of 10 mg/l of bovine serum albumin (BSA), were bound according to the invention to silica particles, and for comparison to ESTAPOR®-NH$_2$ particles (amino-derivatized, crosslinked organic polymer). The reaction is started by the addition of the particles; the measured value for 0 minutes is determined before addition of the particles. By measurement of the radioactivity in the supernatant, the binding kinetics are determined; the radioactivity in the supernatant is indicated:

| Time | According to the invention | | Organic polymer | |
|---|---|---|---|---|
| | (cpm/1000) | | | |
| (min) | without BSA | with BSA | without BSA | with BSA |
| 0 | 91 | 94 | 91 | 93 |
| 1 | 14 | 14 | 48 | 33 |
| 5 | 5 | 1 | 25 | 22 |
| 10 | 3 | 1 | 13 | 10 |
| 15 | 4 | 1 | 9 | 8 |
| 30 | 4 | 1 | 7 | 7 |
| 60 | 4 | 1 | 4 | 3 |
| 120 | 4 | 1 | 3 | 2 |

It is seen that, in the process according to the invention, the saturation range for the binding of the nucleic acid is achieved even after 5 to 10 minutes and a reproducible binding behaviour is thus achieved after 5 to 10 minutes. When using a support according to the prior art (organic amino-substituted polymer), this is only achieved after one to two hours.

BRIEF DESCRIPTION OF THE DRAWINGS

The values of the above table are presented in FIG. 1. For the individual series of measurements, to this end the percentage proportion of the radioactivity bound to the support was determined from the respective radioactivity in the supernatant and the $t_0$ value.

Figure 1:
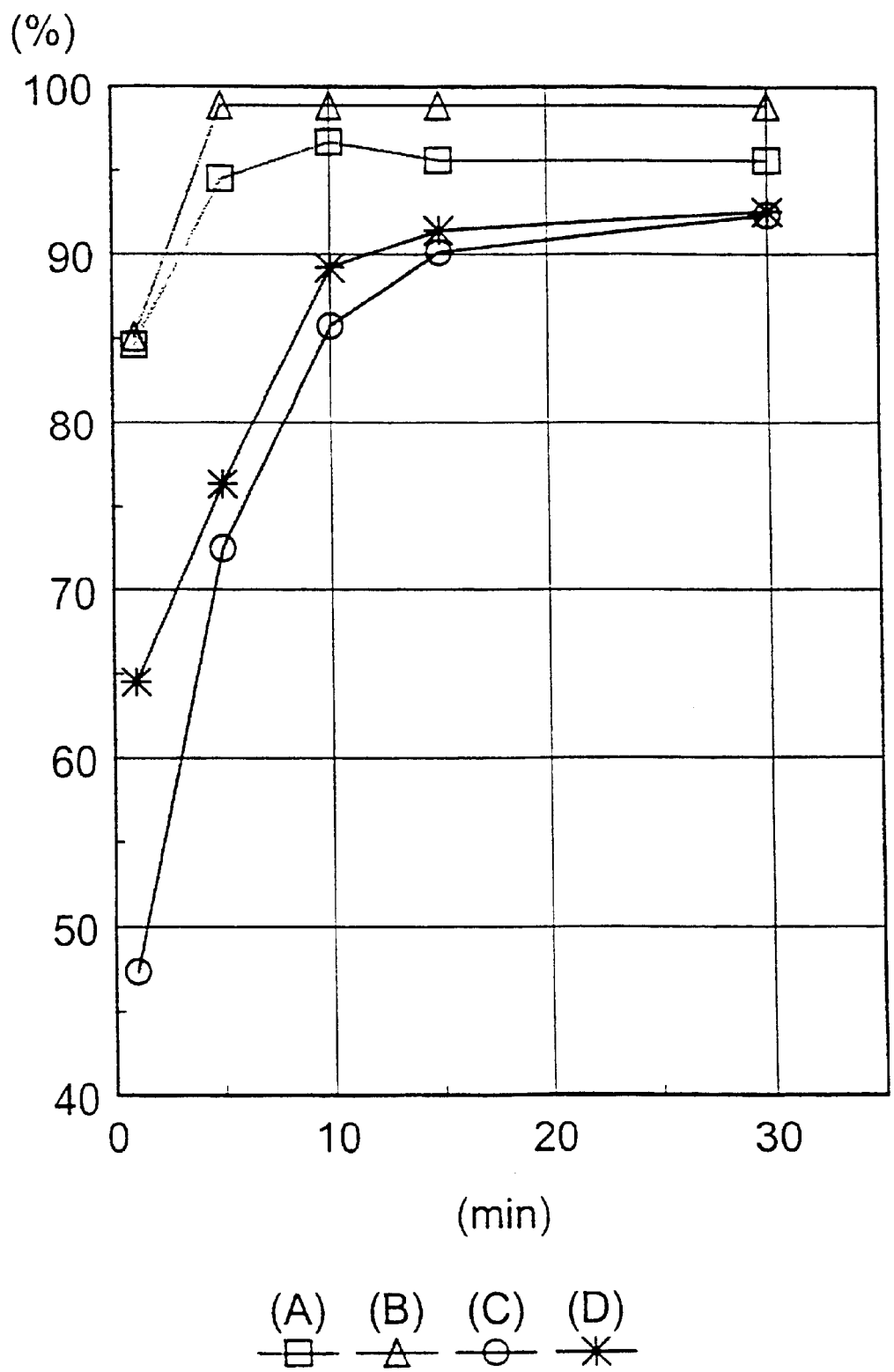

What is claimed is:

1. A process for the isolation and purification of nucleic acids from a liquid sample, comprising:
   (a) providing a liquid sample which contains nucleic acids;
   (b) providing a carrier comprising an inorganic oxide material containing hydroxyl groups;
   (c) diluting the sample from step (a) with an acid binding buffer such that the sample is acidified by the binding buffer;
   (d) treating the sample from (c) with the carrier from (b) so that the nucleic acids become bound to said carrier, with the proviso that the binding buffer is essentially free of ions in concentrations >200 mM, ionic detergents and chaotropic substances;
   (e) separating the carrier with the bound nucleic acids from the rest of the sample and the binding buffer; and
   (f) eluting nucleic acids bound to the carrier in (d) with an alkaline solution.

2. The process according to claim 1, wherein a washing step (e1) is carried out after step (e) with a wash buffer having a pH of ≦6.5.

3. The process according to claim 1, wherein the binding buffer for step (c) has a pH of 3 to 6.

4. The process according to claim 1, wherein the alkaline solution has a pH of 7.5 to 9.

5. A reagent combination for a process according to claim 1, comprising an acid binding buffer and a carrier material comprising an inorganic oxide material containing hydroxyl groups, said acid binding buffer being essentially free of ions in concentrations >200 mM, ionic detergents and chaotropic agents.

6. A reagent combination for a process according to claim 1, comprising a binding buffer having a pH at 3 to 6 and a carrier material comprising an inorganic oxide material containing hydroxyl groups, said acid binding buffer being essentially free of ion concentrations >200 mM, ionic detergents and chaotropic agents.

7. The process according to claim 1, wherein said carrier is in the form of a bead, particle, sheet, gel, membrane, fiber, capillary, strip, microtitre plate or tube.

8. The process according to claim 7, wherein said particle is a magnetic bead.

9. The process according to claim 1, wherein said carrier is hydroxyapatite or silica gel.

10. The process according to claim 1, wherein said carrier is $SiO_2$ or silica.

11. The process according to claim 10, wherein the $SiO_2$ or silicate is silica gel, Kieselguhr, silicate glass or zeolite.

* * * * *